United States Patent
Appling et al.

(10) Patent No.: US 7,458,967 B2
(45) Date of Patent: Dec. 2, 2008

(54) ENDOVASCULAR TREATMENT APPARATUS AND METHOD

(75) Inventors: William M. Appling, Granville, NY (US); Lowell S. Kabnick, Far Hills, NJ (US)

(73) Assignee: AngioDynamics, Inc., Queensbury, NY (US)

( * ) Notice: Subject to any disclaimer, the term of this patent is extended or adjusted under 35 U.S.C. 154(b) by 506 days.

(21) Appl. No.: 10/836,084

(22) Filed: Apr. 30, 2004

(65) Prior Publication Data

US 2005/0096642 A1    May 5, 2005

Related U.S. Application Data

(60) Provisional application No. 60/516,156, filed on Oct. 31, 2003.

(51) Int. Cl.
   *A61B 18/18*    (2006.01)
(52) U.S. Cl. .............. 606/15; 606/7; 600/101
(58) Field of Classification Search ........ 606/7, 606/13–16; 607/88, 89; 601/101, 103–106, 601/114
   See application file for complete search history.

(56) References Cited

U.S. PATENT DOCUMENTS

| | | | |
|---|---|---|---|
| 3,605,750 A | 9/1971 | Sheridan et al. | |
| 4,697,595 A | 10/1987 | Breyer et al. | |
| 5,342,383 A | 8/1994 | Thomas | |
| 5,456,680 A * | 10/1995 | Taylor et al. | 606/2 |
| 5,643,251 A * | 7/1997 | Hillsman et al. | 606/7 |
| 5,693,043 A * | 12/1997 | Kittrell et al. | 606/15 |
| 5,695,482 A * | 12/1997 | Kaldany | 604/526 |
| 5,700,243 A * | 12/1997 | Narciso, Jr. | 604/102.01 |
| 6,056,743 A * | 5/2000 | Ellis et al. | 606/15 |
| 6,126,654 A | 10/2000 | Giba et al. | |
| 6,551,302 B1* | 4/2003 | Rosinko et al. | 604/505 |
| 2002/0072680 A1* | 6/2002 | Schock et al. | 600/486 |
| 2003/0050686 A1* | 3/2003 | Raeder-Devens et al. | 623/1.11 |
| 2003/0199860 A1 | 10/2003 | Loeb et al. | |
| 2004/0093044 A1* | 5/2004 | Rychnovsky et al. | 607/88 |
| 2007/0073160 A1* | 3/2007 | Imam | 600/476 |

FOREIGN PATENT DOCUMENTS

| | | |
|---|---|---|
| DE | 89 05 642 | 10/2003 |
| GB | 1533204 | 11/1978 |

* cited by examiner

*Primary Examiner*—Ahmed M Farah
(74) *Attorney, Agent, or Firm*—Abelman Frayne & Schwab; Harry K. Ahn

(57) ABSTRACT

An endovascular sheath device for use with a thermal treatment apparatus is provided. The device includes a longitudinal tube which is designed to receive a thermal treatment device and is designed to be inserted into a blood vessel. An ultrasonically visible reinforcement element is disposed along the length of the longitudinal tube. The reinforcement element such as a braided wire provides several functions including increased visibility under ultrasound, clearer identification of sheath tip, and increased durability to protect the fiber from needle punctures during tumescent injections into the perivenous space. The wire reinforcement also increases shaft torquability and kink resistance during sheath insertion and withdrawal.

14 Claims, 6 Drawing Sheets

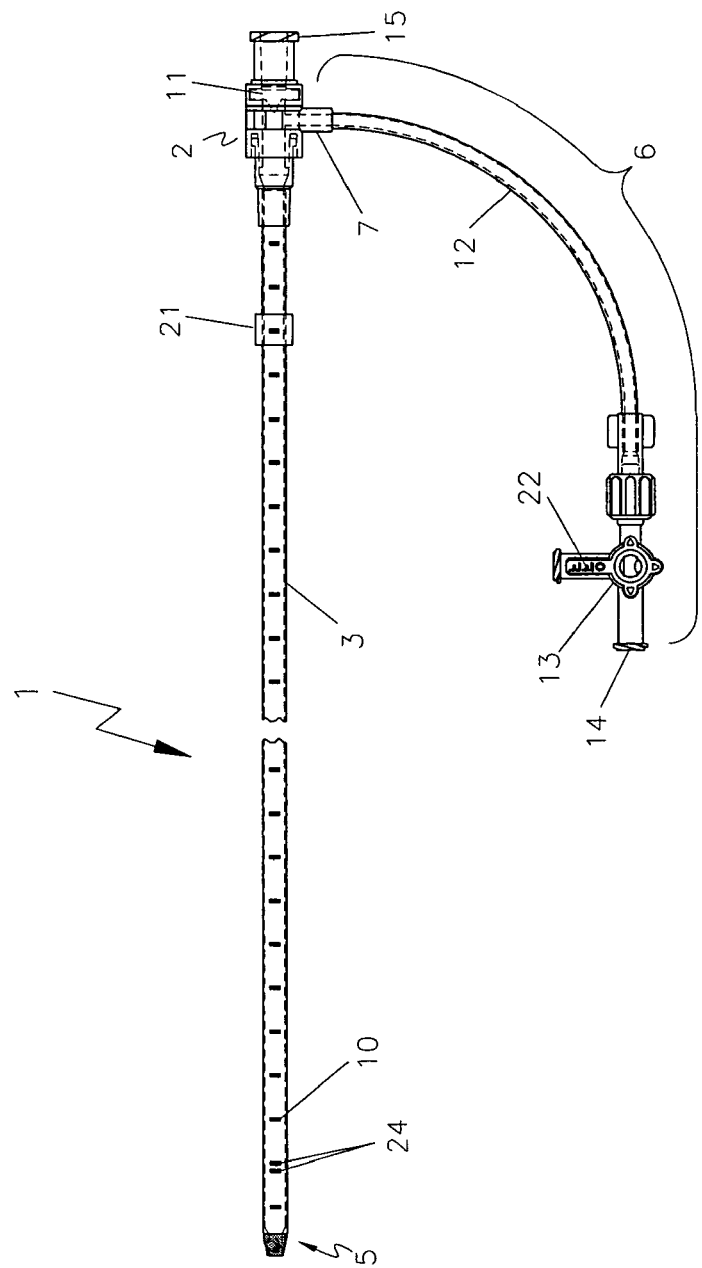
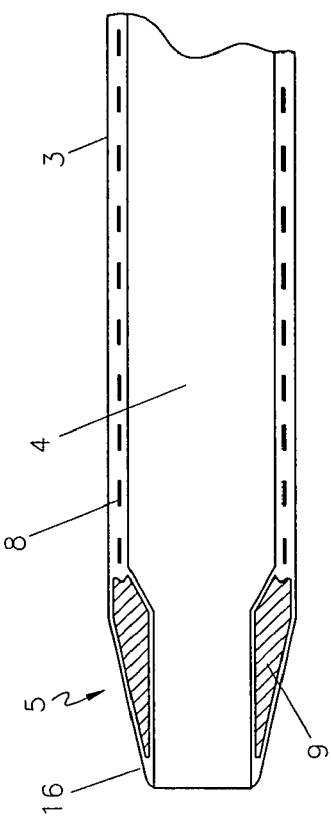
FIG. 1
FIG. 2

ENDOVASCULAR TREATMENT APPARATUS AND METHOD

CROSS REFERENCE TO RELATED APPLICATIONS

This application claims priority to U.S. provisional application No. 60/516,156, filed Oct. 31, 2003, which is incorporated into the present specification by reference.

FIELD OF THE INVENTION

The present invention relates to a medical device apparatus and method for treatment of blood vessels. More particularly, the present invention relates to an endovascular sheath apparatus and method for minimally invasive treatment of venous reflux disease.

BACKGROUND OF THE INVENTION

Veins can be broadly divided into three categories: the deep veins, which are the primary conduit for blood return to the heart; the superficial veins, which parallel the deep veins and function as a channel for blood passing from superficial structures to the deep system; and topical or cutaneous veins, which carry blood from the end organs (e.g., skin) to the superficial system. Veins are thin-walled and contain one-way valves that control blood flow. Normally, the valves open to allow blood to flow into the deep veins and close to prevent back-flow into the superficial veins. When the valves are malfunctioning or only partially functioning, however, they no longer prevent the back-flow of blood into the superficial veins. This condition is called reflux. As a result of reflux, venous pressure builds within the superficial system. This pressure is transmitted to topical veins, which, because the veins are thin walled and not able to withstand the increased pressure, become dilated, tortuous or engorged.

In particular, venous reflux in the lower extremities is one of the most common medical conditions of the adult population. It is estimated that venous reflux disease affects approximately 25% of adult females and 10% of males. Symptoms of reflux include varicose veins and other cosmetic deformities, as well as aching, itching, and swelling of the legs. If left untreated, venous reflux may cause severe medical complications such as bleeding, phlebitis, ulcerations, thrombi and lipodermatosclerosis.

Endovascular thermal therapy is a relatively new treatment technique for venous reflux diseases. With this technique, thermal energy generated by laser, radio or microwave frequencies is delivered to the inner vein wall causing vessel ablation or occlusion. Typically a catheter, fiber or other delivery system is percutaneously inserted into the lumen of the diseased vein. Thermal energy is delivered from the distal end of the delivery system as the device is slowly withdrawn through the vein. Although the device description described herein focuses on endovenous treatment using laser energy, other thermal energy forms may be used.

The procedure begins with an introducer sheath being placed into the main superficial vein, called the great saphenous vein, at a distal location and advanced to within a few centimeters of the point at which the great saphenous vein enters the deep vein system, (the sapheno-femoral junction). Typically, a physician will measure the distance from the insertion or access site to the sapheno-femoral junction on the surface of the patient's skin. This measurement is then transferred to the sheath using tape, a marker or some other visual indicator to identify the insertion distance on the sheath shaft. Other superficial veins may be accessed depending on the origin of reflux.

The sheath is placed using either ultrasonic guidance or fluoroscopic imaging. The physician inserts the sheath into the vein using the visual mark on the sheath as an approximate insertion distance indicator. Ultrasonic or fluoroscopic imaging is then used to guide final placement of the tip relative to the junction. Positioning of the sheath tip relative to the sapheno-femoral junction or other reflux point is critical to the procedure because the sheath tip position is used to confirm correct positioning of the fiber when it is inserted and advanced. Current art sheath tips are often difficult to clearly visualize under either ultrasonic guidance or fluoroscopic imaging.

Once the sheath is properly positioned, a flexible optical fiber is inserted into the lumen of the sheath and advanced until the fiber tip is near the sheath tip but still protected within the sheath lumen. The fiber includes a red aiming beam at the tip that is used to visualize the location of the fiber tip within the vessel lumen as it is advanced to the sapheno-femoral junction through the properly positioned sheath lumen. When activated, the aiming beam appears as a red glowing light visible through the skin surface. One problem with the use of a conventional sheath is that the sheath material often blocks the red aiming beam from being clearly visible on the skin surface as the fiber is advanced through the sheath.

Prior to the application of thermal energy, tumescent anesthesia is injected along the entire length of the vein into space between the vein and the surrounding perivenous tissue. A mixture of saline and 0.1-0.5% lidocaine or other similar anesthetic agent is typically used. Tumescent anesthesia serves several functions. The fluid anatomically isolates the vein, creating a barrier to protect the tissue and nerves from the thermal energy. Specifically, the fluid provides a heat sink to prevent thermal injury to adjacent non-target tissues, nerves and the skin surface. Extrinsic pressure from the fluid also compresses the vessel, reducing the vein diameter, minimizing the volume of the vein, and maximizing the heat affect to the vein walls. Finally, the lidocaine mixture, with its anesthetic characteristics, reduces patient pain during the procedure.

The tumescent injections are typically administered every few centimeters along the entire length of the vein under ultrasonic guidance. Ultrasound is used to visualize the vein, confirm proper location of the needle tip in the perivenous space, and to determine correct injection volumes. After the user has confirmed that the needle tip is correctly positioned between the vein and perivenous tissue through ultrasonic imaging, the tumescent fluid is slowly injected. Again, visualization of the target perivenous space is often difficult, and the user may inadvertently puncture the sheath wall with the needle tip during placement. The delicate fiber may also be damaged by incorrect placement of the needle.

Once the combined sheath/optical fiber assembly is properly positioned and after the administration of tumescent anesthesia as described above, thermal energy can be applied to the vein. To treat the vein, a laser generator is activated causing energy to be emitted from the distal end of the optical fiber into the vessel. The energy reacts with the blood remaining in the vessel and causes heat, which damages the vein wall which, in turn, causes cell necrosis and eventual vein collapse. With the energy source turned on, the sheath and fiber are slowly withdrawn as a single unit until the entire diseased segment of the vessel has been treated.

Currently available sheaths for endovascular laser treatment of reflux have several drawbacks. One problem is the difficulty in visualizing the sheath and particularly the tip as it is positioned just proximal to the sapheno-femoral junction. Although some currently available sheaths may be visible under fluoroscopic guidance, these same sheaths are not optimized for use with ultrasonic imaging modalities. The visibility of the tip under either fluoro or ultrasound is very important when placing the tip relative to the sapheno-femoral junction. Incorrect placement may result in either incomplete occlusion of the vein or non-targeted thermal energy delivery to the femoral vein, which may result in deep vein thrombosis and its associated complications including pulmonary embolism. Another possible complication of a misplaced device is possible vessel perforation.

Another problem with conventional sheaths is that they have shaft colorant. The colorant results in difficulty visualizing the red aiming beam on the skin surface due to partial or complete blocking of the beam by the colored material.

Sheaths that are sold with endovascular laser treatment kits do not contain any shaft reinforcement to increase torquability, durability and kink resistance during insertion and placement within the vein. A reinforced sheath shaft is also desirable to provide a durable, protective barrier to the delicate fiber during tumescent injections, which are administered along the length of the vessel being treated.

Most prior art sheaths do not include any measurement indicator for the physician to determine the approximate length the sheath should be inserted into the vein to be positioned just proximally of the sapheno-femoral junction. Without any measurement indicator, the physician must manually mark the sheath's surface using adhesive tape or other means to indicate maximum insertion length. In addition, most prior art sheaths do not provide a simple, easy mechanism for determining the rate at which the sheath/optical fiber assembly should be withdrawn through the vein during the actual treatment step.

Therefore, it is desirable to provide an endovascular treatment sheath and method that provides for optimized visibility under fluoroscopic imaging or ultrasound imaging or preferably under both. The sheath should be designed to provide easy visual identification of the sheath location for precise positioning relative to the sapheno-femoral junction or other vessel target. Specifically, the sheath tip should be easily visible under either ultrasound or fluoroscopic imaging. The sheath should not block or decrease visibility of the aiming beam during fiber insertion through the sheath. The sheath should also be durable and resistant to needle punctures. The sheath should also be constructed to optimize torquability and kink-resistance during insertion and withdrawal. The device should also provide an easy, simple way for the physician to approximate insertion length and assess pullback rate during the procedure. In addition, the device should be easy and inexpensive to use.

SUMMARY OF THE DISCLOSURE

According to the principles of the present invention, an endovascular sheath device for use with a thermal treatment apparatus is provided. The sheath device includes a longitudinal tube which is designed to receive a thermal treatment device and is designed to be inserted into a blood vessel. An ultrasonically visible reinforcement element is disposed along a wall of the longitudinal tube. The reinforcement element such as a braided wire provides several functions including increased visibility under ultrasound, clearer identification of sheath tip, and increased durability to protect the fiber from needle punctured during tumescent injections into the perivenous space. The wire reinforcement also increases shaft torquability and kink resistance during sheath insertion and withdrawal.

In one aspect of the invention, the longitudinal tube includes a radiopaque tip at its distal end which is fluoroscopically visible. The tip, for example, may include a radiopaque filler such as Tungsten or Barium Sulfate for increased visibility under fluoroscopic imaging. In addition, since the radiopaque filler is generally non-translucent, the radiopaque tip can be more easily seen as it exits the puncture site. This serves as an indicator that the energy emitting section of the fiber is close to the exit site and that the treatment procedure is nearing an end.

In another aspect of the invention, the longitudinal tube is made of a translucent material to provide a user with an improved visibility to the red aiming beam of the optical fiber when the fiber is being inserted through the sheath.

In another aspect of the invention, spaced apart distance marks are provided on the longitudinal tube to provide the user with an easy method of determining the approximate insertion distance of the sheath. These same mark can be also used to assess and adjust pullback rates during withdrawal of the sheath through the vein.

In another aspect of the invention, an adjustable depth stop slidably arranged on the sheath shaft provides a simple, easy way for the user to mark insertion depth and to adjust the sheath position after tumescent injections, if necessary. Accordingly, the adjustable depth stop on the sheath eliminates the time-consuming and inaccurate steps of manually marking the sheath surface prior to insertion into the vein and adjusting sheath position after the tumescent injections.

Thus, the present sheath device eliminates many of the problems that exist with current art sheaths. The present device allows the user the option of using either fluoroscopic or ultrasound imaging modalities or a combination of both during the thermal laser procedure. The present sheath device provides increased visibility of not only the shaft with its ultrasonically visible reinforcement element but also increased fluoroscopic visibility of the sheath tip. The present device eliminates the time-consuming and often inaccurate process of manually marking the sheath insertion distance. The sheath is easily inserted, advanced and withdrawn due to the torquability and kink-resistance features associated with the reinforcement element. The reinforced shaft also provides an ultrasonically visible target during the perivenous injections of tumescent fluids as well as added protection against damage from needle sticks during tumescent injections. Visual distance marks on the longitudinal tube provide the user with an easy method of withdrawing the device at a consistent rate. The adjustable depth stop feature of the present sheath device provides a positioning indicator as well as a retention function to prevent the sheath from moving out of position during the injection of tumescent fluids or during other procedural steps.

BRIEF DESCRIPTION OF THE DRAWINGS

FIG. 1 is a plan view of one embodiment of an endovascular laser treatment sheath according to the present invention.

FIG. 2 is a partial cross-sectional view of the distal section of the endovascular laser treatment sheath of the present invention.

DETAILED DESCRIPTION OF THE INVENTION

Figure 3:
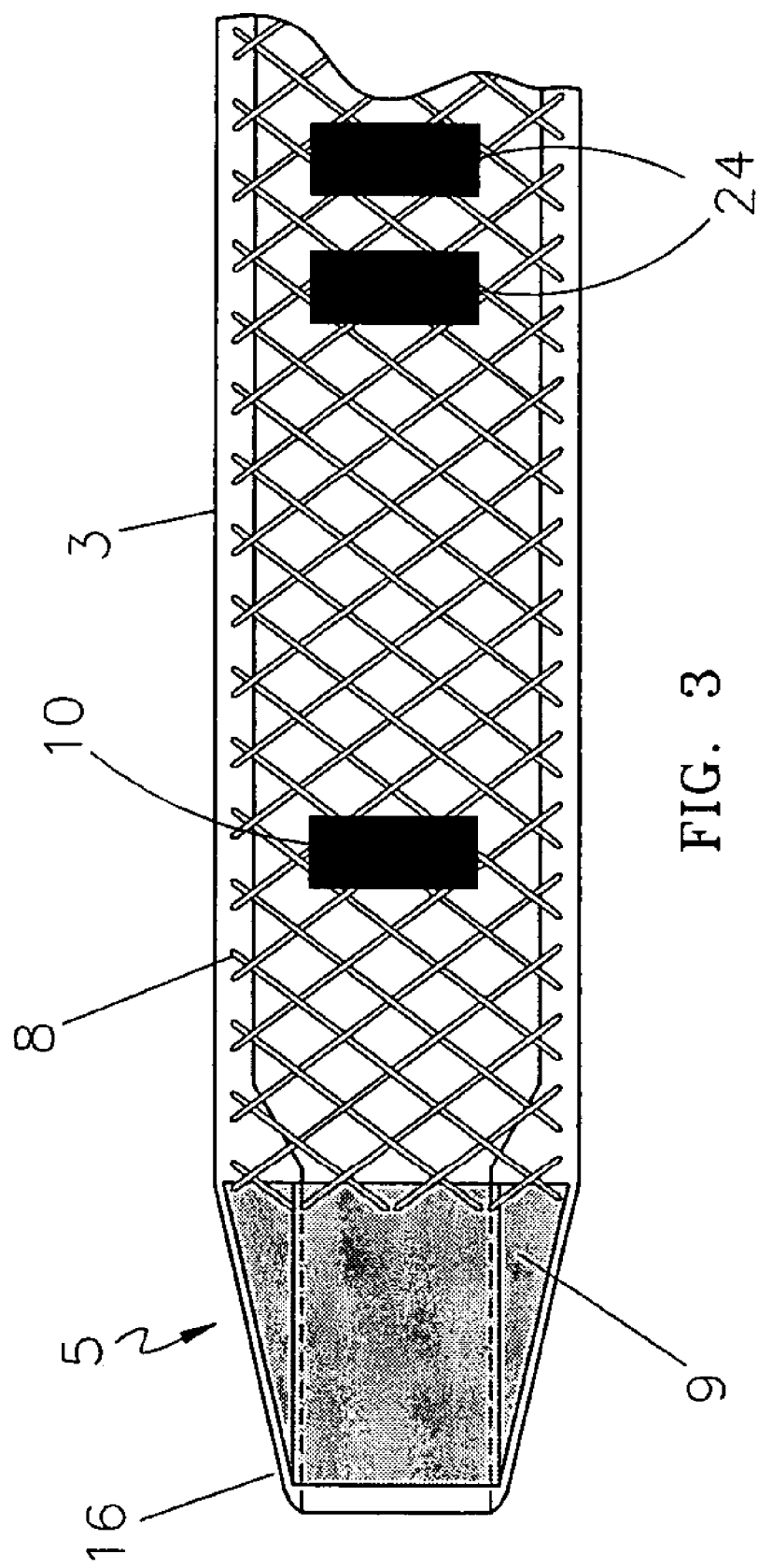
FIG. 3 is a partial plan view of the distal section of the endovascular laser treatment sheath of the present invention with a braided reinforced wire.

One embodiment of the present invention is shown in FIG. 1 through FIG. 3. The endovascular laser treatment sheath 1 is comprised of a hub 2, shaft 3 with through lumen 4, and distal tip 5. The hub 2 may include a side arm assembly 6 for infusion or aspiration of fluids during the thermal treatment procedure. The sheath shaft 3 is comprised of a visibly translucent material reinforced with a wire 8 having a predefined pattern such as braided or coil-wound pattern which is embedded within the translucent material, as shown in FIG. 3. The outer wall of the sheath shaft 3 may include distance markers 10. An adjustable depth stop 21 is coaxially and slidably arranged around the sheath shaft 3.

Figure 5:
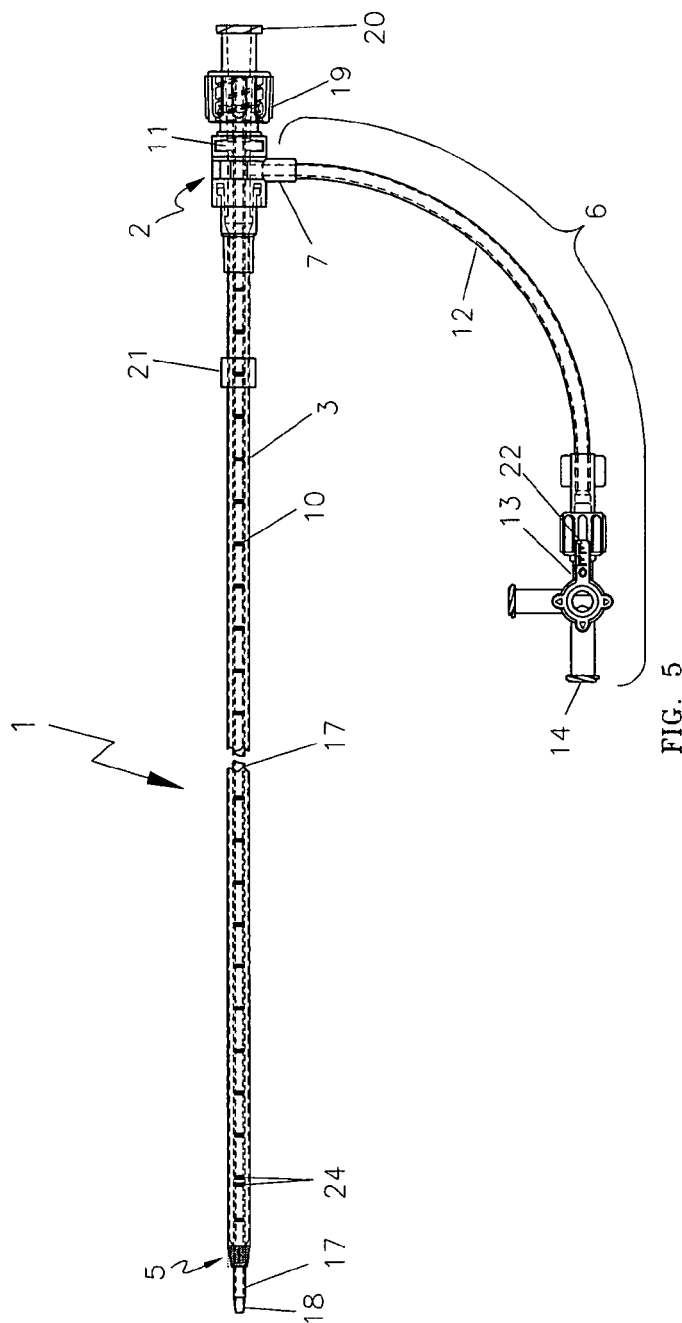
FIG. 5 is a plan view of the endovascular laser treatment sheath of the present invention assembled with a dilator.
Figure 6:
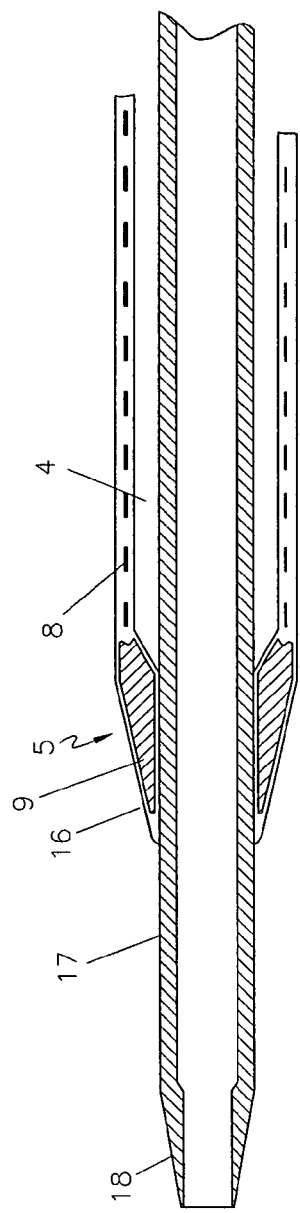
FIG. 6 is a partial cross-sectional view of the distal section of the endovascular laser treatment sheath assembled with the dilator.

The sheath tip 5 has a tapered outer profile as shown in FIG. 2 and FIG. 3. As is well known in the art, the taper provides a smooth transition from the outer diameter of the sheath shaft 3 to the smaller outer diameter of the sheath distal tip. The taper aids in insertion and advancement and also provides an overall tapered profile when assembled with a dilator 17 as shown in FIG. 5 and FIG. 6. The outer diameter of the sheath shaft 3 is approximately 0.079" tapering to approximately 0.058" at the distal end of the sheath tip 5. The sheath has an inner diameter of 0.054" to allow the dilator 17 to be inserted and advanced through the tip 5. The tapered tip section 5 may be as short as practical while ensuring ease of entry and advancement. Optimally, the tapered tip section 5 is 2 mm but may range from 1 to 5 mm in length.

One novel aspect of the current invention is the dual material tip construction. The tip contains a fluoroscopically visible tip core 9 encapsulated within a thin layer of the translucent material 16. The fluoroscopically visible tip core 9 is made of a polymer with radiopaque filler such as tungsten or barium sulfate for increased visibility under fluoroscopic imaging. Alternatively, the tip core 9 may be formed using a metallic band encapsulated within the polymer layer or may be designed with an ultrasonically visible filler such as hollow microspheres which create internal air pockets to enhance the reflective characteristics of the tip. With any of these embodiments, the radiopaque sheath tip provides the physician with the option of positioning the sheath tip within the vessel using fluoroscopic or ultrasonic guidance.

The outer layer 16 of the tip protects the tissue and vessel from the abrasive characteristics of radiopaque filler material. Specifically, the outer tip layer 16 encapsulates the abrasive radiopaque material providing a smooth, low-friction outer surface during insertion, advancement and withdrawal of the device through the vasculature.

Referring now to the sheath shaft 3 depicted in FIG. 1 through FIG. 3, the shaft 3 may be comprised of a translucent material such as nylon or other natural polymer material such as Teflon or polyethylene. Prior art endovascular laser sheaths contain fillers or colorants that partially block the red aiming beam and inhibit optimal visibility. The translucent shaft material of the current invention does not block the beam's emitting light and thus improves the overall visibility of the red aiming beam through the skin surface as the fiber is inserted through the sheath 1 and advanced through the vein.

Figure 4:
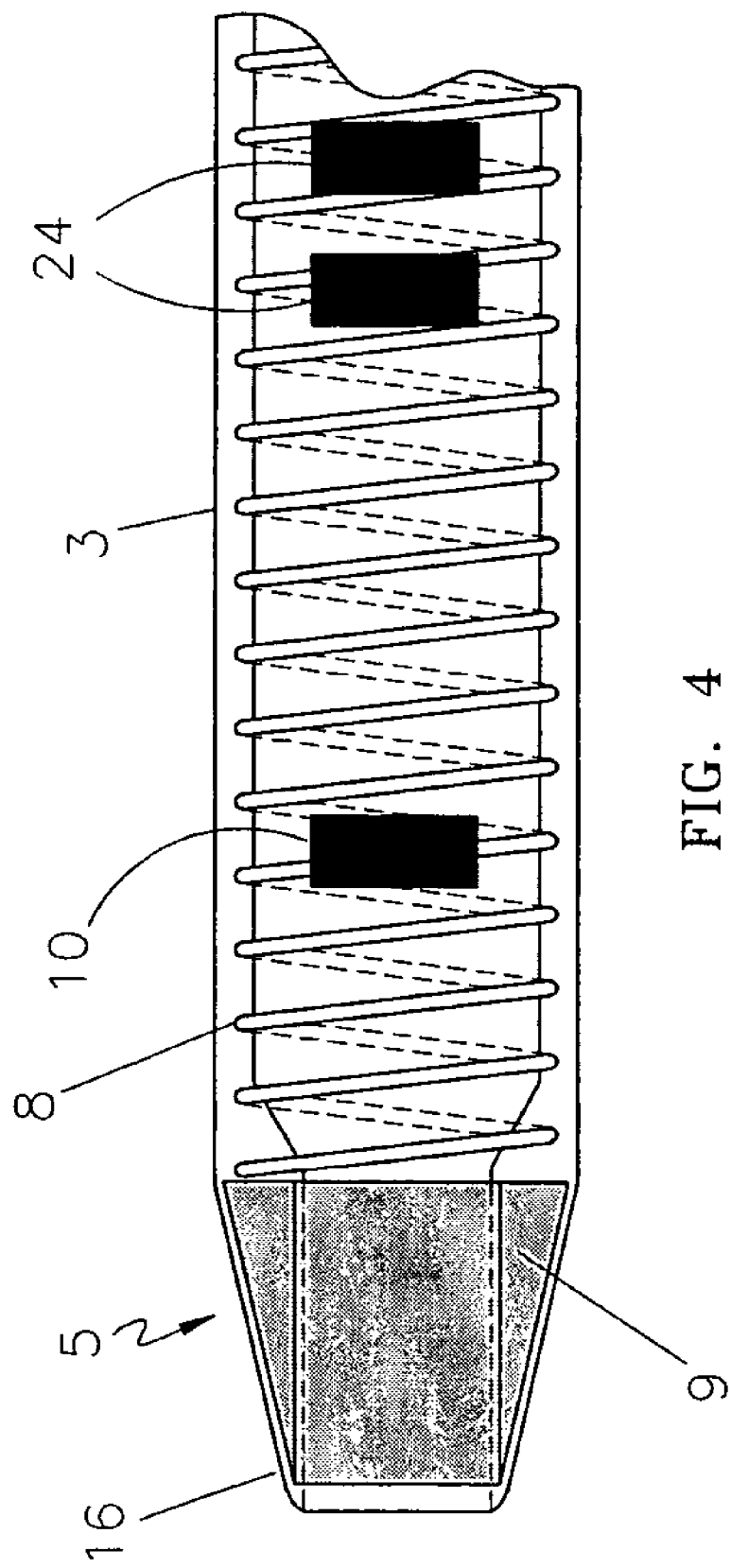
FIG. 4 is a partial plan view of the distal section of the endovascular laser treatment sheath of the present invention with a wound reinforcement wire.

Embedded within the translucent shaft material is a reinforcement element such as a wire 8 having a predetermined pattern such as a braided or wound pattern. FIG. 3 shows the wire 8 in a braided configuration. An alternative coil-wound or helical wire pattern is depicted in FIG. 4. The reinforcing wire 8 is embedded within the translucent shaft material for the entire length of the sheath shaft 3, terminating at the distal tip 5, as shown in FIG. 3 and 4. The wire 8 may be medical grade stainless steel, nitinol or other ultrasonically visible material. Flat wire or round wire may be utilized. The advantage of flat wire includes more reflective surface area for enhanced ultrasonic visibility and a reduced cross-sectional profile. Round wire, on the other hand, is less expensive and easier to manufacture.

The embedded wire 8 provides several key advantages over prior art laser sheaths. It not only serves to enhance shaft visibility under ultrasound imaging, but also provides for an increased maneuverability and kink-resistance during insertion and advancement through the vessel. The wire reinforcement also provides increased durability and resistance against inadvertent needle punctures.

The wire 8 provides a reflective surface for the ultrasonic wave. The speed of the ultrasound changes from media to media. At each change in the speed of sound, a sound wave echo is reflected or returned and captured by the ultrasonic transducer or probe. As the ultrasound wave travels through the skin, tissue, vein and sheath, echoes are returned. When the ultrasound wave contacts the reinforced wire, the change in media causes an echo to be returned to the probe, resulting in an ultrasonic image with enhanced visibility over conventional, non-reinforced sheath designs.

The wire 8 reinforced shaft provides enhanced maneuverability during insertion and advancement through the target vessel. As is well known in the art, shaft material reinforced with an embedded wire pattern increases torquability, (rotation force) and pushability. Thus, the wire design provides the user with enhanced control over the sheath's advancement and positioning. Wire reinforcement also provides increased resistance to kinking of the shaft during insertion and advancement.

During the injection of tumescent fluids, as will be described more fully below, the reinforcement wire 8 provides both increased visibility and durability over currently available sheaths. The reinforcement wire 8, with its increased ultrasonic visibility, provides an easily identifiable target for the physician when inserting and positioning the injection needle within the perivenous space. The wire 8 increases the overall durability of the sheath 1, providing an added barrier to prevent misaligned needle tips from accidentally puncturing and penetrating the sheath shaft 3 during tumescent injections. Accidental puncture could result in the needle tip coming into direct contact with and damaging the fragile optical fiber, and negatively impacting the clinical outcome of the procedure. The combination of improved visibility and durability make it possible to use the sheath shaft 3 as a target for tumescent injections without risking damage to the fiber.

Figure 8A:
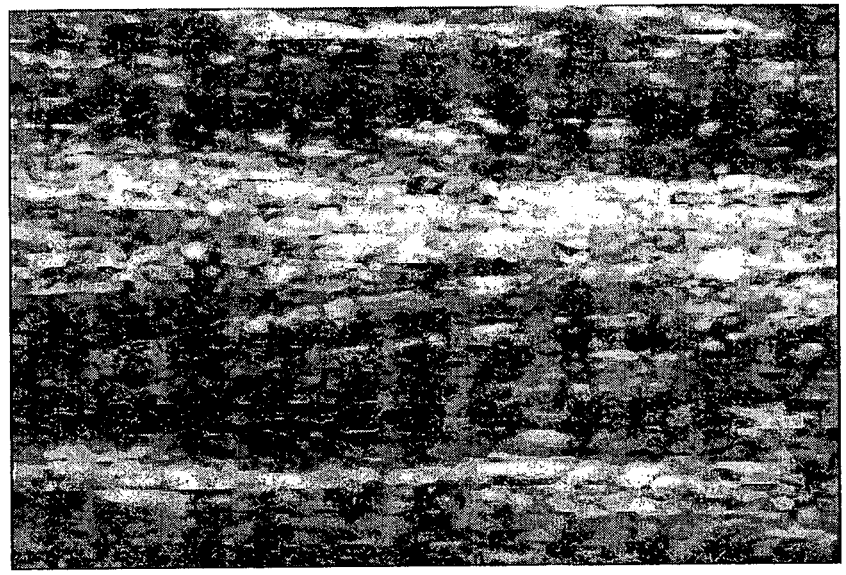
FIG. 8A shows an ultrasound image of a conventional sheath positioned in a vessel and FIG. 8B shows an ultrasound image of a sheath positioned in a vessel according to the present invention.
Figure 8B:
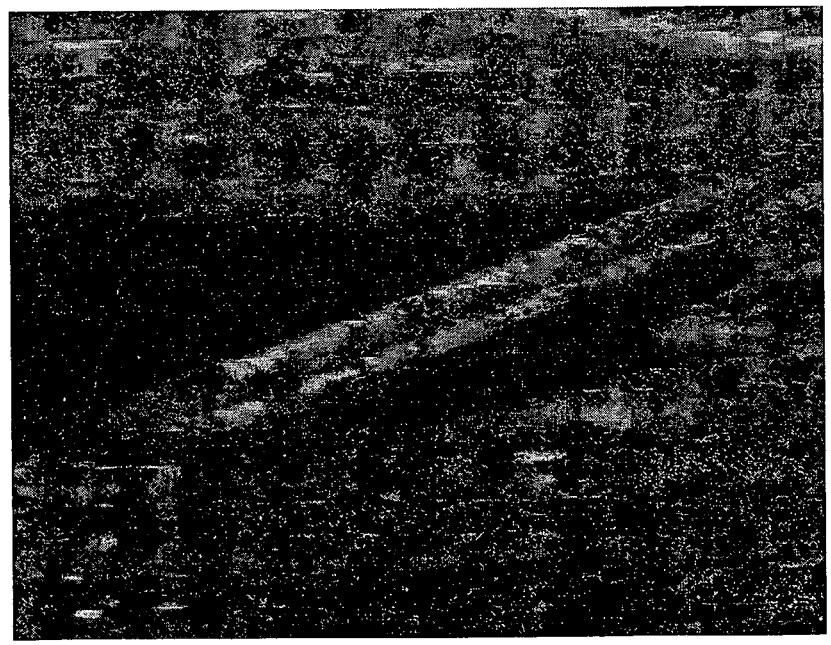

As shown in FIG. 3 and FIG. 4, the transition between the sheath tip 5 and the distal end of the reinforcing wire 8 provides a visual landmark for the physician during placement of the tip 5 relative to the sapheno-femoral junction. Using either ultrasound or fluoroscopy, the physician can obtain a visual image clearly demarking where the sheath tip 5 ends and the reinforced wire 8 shaft begins. Under ultrasound, the distal end of the reinforcing wire provides a landmark for the physician. The visual effects of the ultrasonically visible reinforcing wire 8 during placement is shown in FIGS. 8A and 8B. FIG. 8A shows an ultrasound image of a conventional sheath positioned in a vessel and FIG. 8B shows an ultrasound image of a sheath positioned in a vessel according to the present invention. As can be seen, the sheath and the sheath tip according to the invention in FIG. 8B is much more visible than the prior art sheath in FIG. 8A. Alternatively, the sheath tip 5 itself will be ultrasonically visible if designed with embedded hollow microspheres, as previously discussed. Under fluoroscopic guidance, the radiopaque qualities of the tip 5 provides the visual landmark for final positioning prior to the activation of laser energy.

The sheath shaft 3 may optionally include a plurality of visual markings 10 uniformly spaced on the shaft outer surface at pre-determined distances, as illustrated in FIG. 1. The markings provide a visual indication of insertion depth, tip position, and withdrawal rates. The markings 10 are preferably in 1 cm increments along the entire length of the shaft, although other distance increments may be used. The markings may be numbered or otherwise designed to provide the user with an indication as to actual distance from the sheath tip 5. The markings may be positioned around the entire circumference of the sheath shaft 3 or may cover only a portion of the shaft 3 circumference as depicted in FIG. 1.

Typically, as part of the patient preparation, the physician measures on the skin surface the distance from the puncture site to the sapheno-femoral junction or other venous target. The sheath marking 10 corresponding to the physician's measurement then provides an approximate indication as to the length the sheath 1 should be inserted to reach the anatomical target. The markings 10 also provide an approximate indication of sheath tip 5 position within the vessel. As will be explained more fully below, during withdrawal of the combined sheath/optical fiber device, the sheath markings 10 can be used to provide the physician with an indication of pullback rate of the sheath.

Optionally, one of the markings 10 located near the sheath tip 5 may be designed to be visually different from the other markings. This marking 24 provides a unique visual mark to alert the physician that the optical fiber tip is nearing the access tract. Typically, the physician begins to prepare for the end of the procedure when the sheath tip 5 is about 2 centimeters from the access tract. The unique marking 24 at a distance of about 2 centimeters from the sheath tip 5 provides the physician with an indication of the tip position relative to the puncture tract. The unique marking 24 may be in the form of a different color, pattern or shape to distinguish it from other markings.

Figure 7:
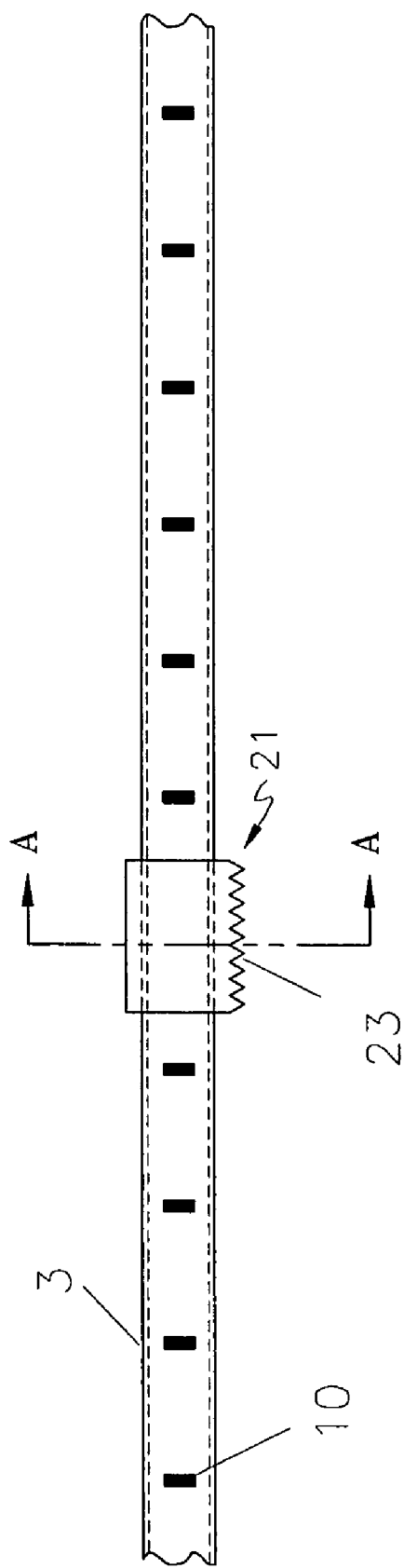
FIG. 7 is a partial plan view of the endovascular laser treatment sheath and a cross-sectional view of the adjustable depth stop coaxially arranged on the sheath.
Figure 7:
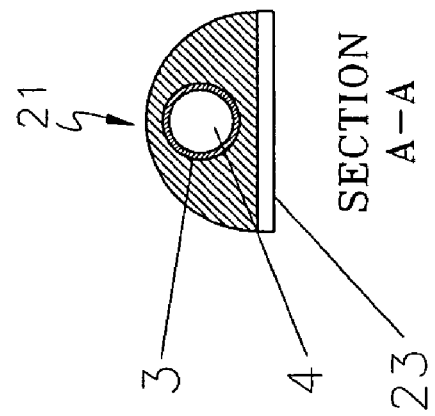

Slidably arranged around the sheath shaft 3 is an adjustable depth indicator 21, shown in FIG. 1 and 7. The depth indicator 21 is a tubular structure made of a flexible, elastomeric material such as silicone. The indicator 21 is dimensioned so that the through hole is slightly smaller than the outer diameter of the sheath shaft 3 yet large enough to be longitudinally slideable along the shaft 3. This interference fit between the shaft 3 and the adjustable depth indicator 21 allows the depth indicator 21 to be manually positioned by the physician. Once positioned, the depth indicator 21 will remain in the set position due to the interference fit or friction with the shaft 3. As will be described in more detail below, the depth indicator 21 provides the physician with an easy and simple method of indicating the location on the shaft where the device 1 exits from the puncture site when positioned just below the sapheno-femoral junction or other reflux point. Like the markings 10 described above, the depth indicator 21 provides an approximate indication as to the length the sheath should be inserted to reach the target position within the vessel.

The adjustable depth stop 21 also performs the function of reducing the risk of longitudinal sheath movement once the device has been positioned. Often, as tumescent injections are administered along the length of the vein, the vein may elongate causing the sheath 1 to slip proximally. The adjustable depth stop 21 may be designed to provide a high friction surface to reduce longitudinal movement of the device during injections or during other procedural steps. As shown in FIG. 7, the adjustable depth stop 21 has an increased skin surface contact area along surface 23. Surface 23 may have textured surface such as a ridged profile as shown in FIG. 7. Using a soft material such as urethane may also generate increased friction. When the adjustable depth stop 21 is positioned on the skin surface at the puncture site, the ridges provide an increased frictional contact surface with the skin that reduces longitudinal movement of the sheath 1. In the event that the sheath 1 does move, the device can be easily repositioned by advancing the sheath 1 into the vein until the adjustable stop 21 once again comes in contact with the skin surface along stop surface 23. Thus, the depth stop 21 provides a positioning function during initial placement, reduces the risk of longitudinal movement of the sheath 1 during the administration of tumescent injections and other procedural steps, and allows for easy repositioning of the device if necessary.

The sheath hub 2 typically includes a hemostasis valve as shown in FIG. 1 and 5. The hub 2 includes a valve gasket 11 that provides a leak-proof seal to prevent the backflow of blood out of the sheath hub 2 opening while simultaneously allowing the introduction of fibers, guidewires and other interventional devices into the sheath 1. The valve gasket 11 is made of elastomeric material, as is commonly found in the art. The gasket 11 opens to receive the optical fiber (not shown) and then seals around the fiber. However, the valve gasket 11 does not open in response to pressure from the distal side in order to prevent the back-flow of blood or other fluids. The gasket 11 also prevents air from entering the sheath through the hub 2. The hub 2 also includes a standard luer threaded proximal end 15 for a threaded connection to a dilator hub 19 or other interventional devices. Although luer threaded hubs are normally used in the medical device industry, any mating connection for connecting two medical components together may be used.

The hub 2 may optionally include a side arm assembly 6 comprised of a side arm port 7, side arm tubing 12 and a three-way stopcock 13. The side arm assembly 6 is used to flush procedural fluids through the sheath lumen 4. The handle 22 on the three-way stopcock 13 controls the fluid path. When the handle 22 is positioned as shown in FIG. 1, fluids injected through the stopcock port 14, flows through the lumen of the side arm tubing 12 and the side arm port 7 into the sheath lumen 4. When the handle 22 is positioned toward the side arm tubing 12 as shown in FIG. 5, backflow of bodily and procedural fluids are prevented from flowing through the stopcock ports.

One commonly administered fluid during an endovascular laser treatment procedure is saline which is used to flush blood from the sheath 1 prior to or after insertion of the optical fiber (not shown). Blood is often flushed from the sheath 1 to prevent adherence of blood to the optic fiber, which can adversely affect the intensity of the laser energy within the vessel. The side arm assembly 6 can also be used to administer emergency drugs directly to the vein or to aspirate fluids from the treatment area.

Referring now to FIG. 5 and FIG. 6, the sheath 1 of the current invention is shown assembled with a standard dilator 17. The function of the dilator 17 is to gradually dilate the insertion site so the sheath 1 can be inserted without damage to the tissue surrounding the access site. The dilator 17 provides a gradual, atraumatic transition from the guidewire diameter, typically 0.035" to the full sheath shaft diameter. The dilator tip gradually tapers upward to a shaft diameter of 0.054". The sheath tip 5 provides the secondary taper transitioning between the full dilator shaft diameter to full sheath shaft 3 diameter, typically 0.079". The dilator 17 is dimensioned to fit within the lumen 4 of the sheath shaft 3. The dilator tip 18, which is tapered inwardly as shown in FIG. 6, is dimensioned to extend beyond the distal tip 5 of the sheath 1 when fully inserted. The distal tip 18 opening of the dilator 17 will accommodate an 0.035" guidewire. At the proximal end of the dilator 17, a male luer fitting 19 provides a connecting means to the sheath hub 2. The female luer 20 provides a similar connecting means for other interventional devices and well as providing access to the dilator lumen through the opening in the female luer 20.

A preferred method of using the endovascular laser sheath apparatus 1 for treating varicose veins will now be described. The treatment procedure begins with the standard pre-operative preparation of the patient as is well known in the art. Prior to the procedure, the patient's diseased venous segments are marked on the skin surface. Typically, ultrasound guidance is used to map the vein from highest reflux or valve incompetence point to the lowest treatment point. An approximate measurement of distance from the access site to the highest point of reflux is then obtained. The visual markings 10 on the sheath shaft 3 are then used to locate the corresponding distance from the sheath tip 5 to the marking corresponding to the anatomical measurement. When the sheath 1 is fully inserted and positioned at the target location, the designated marking 10 on the sheath shaft 3 will be positioned at the puncture or access site, thus providing the physician with an approximate indication of insertion depth.

Alternatively, the adjustable depth stop 21 can be positioned on the sheath shaft 3 at the approximate location representing the approximate length of sheath insertion from the distal tip 5. After locating the correct position on the sheath, the user simply slides the depth stop 21 to the identified position while holding the sheath 1 stationary.

After the vein has been marked out and the approximate depth location on the sheath 1 has been identified, the target vein is accessed using a standard Seldinger technique. Under ultrasonic or fluoroscopic guidance, a small gauge needle is used to puncture the skin and access the vein. A guide wire is advanced into the vein through the lumen of the needle. The needle is then removed leaving the guidewire in place. The sheath 1/dilator assembly shown in FIG. 5 is introduced into the vein over the guidewire and advanced to 1 to 2 centimeters below the point of reflux, typically sapheno-femoral junction. Positioning is confirmed using either ultrasound or fluoroscopic imaging. FIG. 8A shows an ultrasound image of a conventional sheath positioned in a vessel. The image is blurred and it is difficult for a user to locate the tip. By contrast, FIG. 8B illustrates an ultrasound image of the sheath positioned in a vessel according to the present invention, which clearly shows the sheath and its tip. Although FIG. 8B shows an ultrasound image, the sheath tip 5 of the current invention is designed to be clearly visible under either imaging technique. Using ultrasound, the distal end of the rein- forcing wire creates a distinguishing echo, enhancing visibility. Optimally, the internal hollow microspheres embedded in the shaft tip 5 core provide enhanced ultrasonic visibility. If fluoroscopic guidance is used, the radiopaque sheath tip is clearly visible.

Once correct positioning of the sheath tip 5 has been confirmed, the guide wire and dilator 17 are removed leaving the sheath 1 in place. The distal end of the optical fiber is then inserted into and is advanced through the sheath 1 until the optical fiber emitting end is flush with the sheath tip 5. The red aiming beam feature of the optical fiber is then activated to track progress through the vein. The translucent nature of the sheath shaft 3 improves the aiming beam visibility during advancement of the optical fiber through the sheath lumen 4. Correct positioning of the sheath tip 5 and fiber tip approximately 1-2 centimeters below the sapheno-femoral junction or other reflux point is once again confirmed using ultrasound or fluoroscopy. At this point, any required adjustments can be made to the overall device position using the sheath tip 5 and/or reinforced wire 8 as a visual landmark.

In preparation for laser activation, the sheath 1 is retracted while holding the optical fiber stationary. This action causes the optical fiber tip to become exposed by the proper distance of approximately 2 centimeters from the sheath tip 5. Once again the imaging guidance features of the sheath tip 5 can be used to confirm correct positioning of sheath 1 and optical fiber after retraction.

Once the device is positioned correctly within the vein, the tissue immediately surrounding the diseased vessel segment is treated with percutaneous infusions of a tumescent anesthetic agent. The physician inserts a small gauge needle through the skin near the puncture site and into the perivenous space between the vein and the surrounding tissue. If ultrasonic guidance is used, the ultrasound probe is placed on the skin in the proximity of puncture to provide an image of the needle position in the perivenous space. The reinforcing wire 8 within the sheath shaft 3 provides an enhanced ultrasonic image of the target area. The physician can use the wire 8, which is clearly visible under ultrasound, to accurately guide and position the needle tip in the perivenous space.

Not only does the wire 8 provide a visually enhanced image, but it also provides added protection to the device in the event of inadvertent needle puncture of the sheath 1. Specifically, the reinforcing wire 8 provides an enhanced protective barrier between the fragile optical fiber and the mis-placed needle tip. If the needle tip punctures the sheath shaft 3, the wire reinforcement 8 provides a physical obstruction to needle advancement, thus reducing the risk of optical fiber damage by the needle tip.

Once the needle tip is positioned within the perivenous space, tumescent injection is administered and the needle is removed. The needle is then repositioned in another location. The procedure is repeated until tumescent fluid has been delivered along the entire length of the vein segment being treated. Typically between 5 and 15 separate needle punctures are required to sufficiently anesthetize the area and create a sufficient fluid barrier for treatment. The total volume of tumescent fluid injected along the vein depends on the concentration of lidocaine used. For example, if a solution of 0.25% lidocaine is used, up to a maximum of 200 cc may be injected along the course of the vein. Regardless of the concentration used, multiple injections are required. Visibility of the target area is greatly enhanced by the reflective characteristics of the sheath's wire 8 reinforcement, thus reducing the chance of misplacing the needle tip during any of the numerous needle punctures required to completely administer tumescent fluids.

The adjustable depth stop 21, with its increased skin surface contact area along surface 23 (FIG. 7), minimizes sheath 1 movement during the tumescent injection. The depth stop 21 may be used to confirm that the sheath 1 has not slipped proximally during the injections of tumescent anesthesia. If necessary, the sheath 1 can be easily repositioned by advancing it into the vein until the adjustable stop 21 once again comes in contact with the skin surface in the area of the access site. Thus, the depth stop 21 reduces the risk of longitudinal movement of the sheath 1 during pre-procedure preparation and during the procedure itself. The stop 21 also provides the physician with an easy method of repositioning the sheath if necessary.

Once the vein has been sufficiently anesthetized, laser energy is applied to the interior of the diseased vein. The laser generator is activated and the combined sheath 1/optical fiber is then slowly withdrawn as a single unit through the vein, preferably at a rate of 2-3 millimeters per second. The laser energy travels down the optical fiber through the tip of the optical fiber and into the vein lumen, where it creates hot bubbles of gas in the bloodstream. The gas bubbles expand to contact the vein wall, along a 360-degree circumference, thus damaging vein wall tissue, and ultimately causing collapse of the vessel.

The physician manually controls the rate at which the sheath 1/optical fiber is withdrawn. As an example, to treat a 45 centimeter vein normally takes approximately 3 minutes, requiring a pullback rate of about one centimeter every four seconds. The markings 10 on the sheath 1 can be used to assist the physician in maintaining an accurate and consistent withdrawal rate. Specifically, the physician can adjust the rate of withdrawal by monitoring the appearance of markings 10 at the puncture site within a particular time period, and adjusting the pullback rate accordingly.

The procedure for treating the varicose vein is considered to be complete when the desired length of the target vein has been exposed to laser energy. Normally, the laser generator is turned off when the fiber tip is approximately 3 centimeters from the access site. The physician can monitor the location of the tip relative to the puncture site in two different ways. The markings 10 on the surface of the sheath 1 as they become visible at the puncture site during pullback can be used to determine the location of the distal tip 5. The appearance at the access site of the unique marking 24 may also be used to determine the location of the sheath tip 5 and to alert the physician that the procedure is almost complete.

Once the physician has been alerted to the proximity of the sheath tip at the access site, the physician continues to pull back the device until the sheath tip 5, with its distinctive color, appears at the access site. When the fiber is in the active or exposed position, the distal end of the fiber typically extends 2 to 2.5 cm beyond the sheath tip 5. When the colored sheath tip 5 appears at the access site, the fiber tip emitting end will be approximately 3 centimeters below the skin opening. At this point, the generator is turned off and the combined sheath 1/optical fiber device can then be removed from the body as a single unit. Thus, the appearance of the colored sheath tip at the puncture site provides a visual signal to the physician that the entire vein segment has been treated and the laser energy can be turned off.

The invention disclosed herein has numerous advantages over prior art treatment devices and methods. The endovascular sheath apparatus and method for venous reflux treatment of the present invention provides for optimized visibility under both fluoroscopic and ultrasonic imaging modalities. The physician has the option of using the same device under either imaging modality. The sheath does not block or decrease the visibility of red aiming beam feature of the laser system because of the translucent shaft material of the sheath. The addition of reinforcing wire to the sheath shaft provides for enhanced visibility and increases overall durability of the device, particularly during multiple tumescent injections with a needle. The wire reinforcement also adds to the maneuverability of the device during insertion, advancement and withdrawal by increasing shaft torquability, pushability and kink-resistance. The device also allows enhanced visibility of the sheath tip leading to increased accuracy during final positioning of the device near the sapheno-femoral junction. Finally, optional markers and the adjustable depth stop provide the user with a simple, yet effective, technique for identifying sheath insertion distances. The depth stop may also act as a retention mechanism to hold the sheath stationary prior to and during the procedure.

Accordingly, important advantages of the endovascular laser sheath system, among others, include increased visibility under imaging, flexibility in the choice of imaging technique, increased control during advancement through the vessel, improved accuracy in placement of the sheath within the vessel, and added protection of the delicate optical fiber during tumescent injections. The invention disclosed herein also increases the physician's ability to maintain a consistent pullback speed during the procedure and to accurately assess when the entire length of the vein has been treated.

The above description and the figures disclose particular embodiments of an endovascular sheath system and method of treatment. It should be noted that various modifications to the device and method might be made without departing from the scope of the invention. The reinforced wire configuration may be of various patterns and wire diameters. Hub fittings other than those specifically described herein are within the scope of this invention. The use of a dilator as described above may not be required. Sheath dimensions may be decreased to accommodate smaller optical fibers such as 400-micron sizes. Endovenous thermal treatment modalities other than laser may be used including microwave or radio-frequency energy. Veins other than the great saphenous vein can be treated using the method described herein. Accordingly, the scope of the invention is not limited to the foregoing specification, but instead is given by the appended claims along with their full range of equivalents.

What is claimed is:

1. An endovascular thermal treatment delivery device comprising:
   a longitudinal tube adapted to receive an optical fiber and adapted to be inserted into a blood vessel and a metallic reinforcement element disposed along the wall of the longitudinal tube, the reinforcement metallic element being ultrasonically visible;
   a tip disposed at a distal end of the longitudinal tube, the tip including one or more air pockets that provide ultrasound visibility.

2. The endovascular thermal treatment delivery device according to claim 1, wherein the longitudinal tube is translucent so as to allow a visual check of an aiming beam to locate an optical fiber tip while the optical fiber is being inserted through the longitudinal tube.

3. The endovascular thermal treatment delivery device according to claim 1, wherein the tip is having a non-translucent radiopaque tip.

4. The endovascular thermal treatment delivery device according to claim 3, wherein the radiopaque tip includes a tapered polymer tip enclosing radiopaque material.

5. The endovascular thermal treatment delivery device according to claim 3 wherein the radiopaque tip is fluoroscopically visible.

6. The endovascular thermal treatment delivery device according to claim 3 wherein the tip attached to the distal end of the tube is ultrasonically visible.

7. The endovascular thermal treatment delivery device according to claim 3 wherein the tip includes a first portion and a second portion having a substantially different density than the first portion.

8. The endovascular thermal treatment delivery device according to claim 7, wherein the one or more air pockets are included in the second portion of the tip.

9. The endovascular thermal treatment delivery device according to claim 8, wherein the one or more air pockets in the second portion include one or more of: voids or hollow microspheres.

10. The endovascular thermal treatment delivery device according to claim 8, wherein the second portion includes metallic material.

11. The endovascular thermal treatment delivery device according to claim 1, further comprising a plurality of distance marks disposed on the longitudinal tube and spaced from each other to facilitate the withdrawal of the device at a consistent rate.

12. The endovascular thermal treatment delivery device according to claim 1, further comprising an adjustable depth stop slidably coupled to the longitudinal tube.

13. The endovascular thermal treatment delivery device according to claim 1, wherein the reinforcement element includes a metallic element having a braided or wound pattern embedded into the longitudinal tube.

14. The endovascular thermal treatment delivery device according to claim 1 wherein the reinforcement element provides increased strength to the longitudinal tube.

* * * * *